United States Patent [19]

Hawari et al.

[11] Patent Number: 5,185,488
[45] Date of Patent: Feb. 9, 1993

[54] PROCESS FOR THE REDUCTIVE DEHALOGENATION OF POLYHALOAROMATICS WITH SODIUM OR CALCIUM IN A LOWER ALCOHOL

[75] Inventors: Jalal A. Hawari, Ville St-Laurent; Réjean Samson, Fabreville Laval, both of Canada

[73] Assignee: Her Majesty the Queen in right of Canada, as represented by the Minister of Natural Resources, Ottawa, Canada

[21] Appl. No.: 538,233

[22] Filed: Jun. 14, 1990

Related U.S. Application Data

[63] Continuation-in-part of Ser. No. 413,942, Sep. 28, 1989, Pat. No. 4,950,833.

[51] Int. Cl.$^5$ .......................... C07C 1/20; C10G 17/00
[52] U.S. Cl. ................... 585/469; 208/262.1; 208/262.5; 423/155; 423/179
[58] Field of Search ............ 585/469; 208/262.1, 208/262.5; 423/155, 179

[56] References Cited

U.S. PATENT DOCUMENTS

| | | | |
|---|---|---|---|
| 4,351,978 | 9/1982 | Hatano et al. | 585/469 |
| 4,447,667 | 5/1984 | Parker et al. | 585/469 |
| 4,776,947 | 10/1988 | Streck et al. | 208/262.1 |
| 4,839,042 | 6/1989 | Tumiatti et al. | 208/262.5 |

FOREIGN PATENT DOCUMENTS 225849  6/1985  European Pat. Off. ............ 585/469

Primary Examiner—Anthony McFarlane
Assistant Examiner—Nhat Phan
Attorney, Agent, or Firm—Ratner & Prestia

[57] ABSTRACT

A process for the reductive dehalogenation of halogenated aromatics. The process comprises reacting halogenated aromatics with sodium or calcium in the presence of a lower alcohol selected from the group comprising methanol, ethanol or isopropanol and mixtures thereof in order to convert the halogenated aromatics to hydrogenated aromatics. The halogenated aromatics are preferably reacted with sodium in the presence of methanol under reaction conditions whereby said sodium is in molten form. The preferred starting sodium/methanol/halogen molar ratio ranges from 30–40/15–20/1. The process is particularly useful for dechlorinating polychlorinated biphenyl found in electrical transformer oil.

10 Claims, No Drawings

PROCESS FOR THE REDUCTIVE DEHALOGENATION OF POLYHALOAROMATICS WITH SODIUM OR CALCIUM IN A LOWER ALCOHOL

CROSS-REFERENCE TO RELATED APPLICATIONS

This application is a continuation-in-part of application Ser. No. 07/413,942, filed Sep. 28, 1989, now U.S. Pat. No. 4,950,833.

FIELD OF THE INVENTION

The present invention relates to a process for the dehalogenation of halogenated aromatics. This process involves reacting halogenated aromatics with sodium or calcium in the presence of a low molecular weight alcohol, preferably methanol.

BACKGROUND OF THE INVENTION

The disposal of halogenated aromatic compounds such as polychlorinated biphenyls (PCBs) has, in recent years, become a problem of growing concern, especially because of the potential environmental hazard resulting from the accumulation of large amounts of such type of compounds.

The use of sodium as a dechlorinating agent for various types of aliphatic and aromatic chlorides is well established and sodium still appears to be the metal of choice in current and future research in the area of PCB treatment. The ultimate purpose of the research done in PCB treatment is obviously to provide effective dechlorination processes that can be carried out safely and efficiently a costs that are as minimal as possible. At the present time, one of the most reliable processes used to dechlorinate PCBs is a process by which the compounds are heated until decomposition occurs. The process involves the use of extremely high temperatures. Among the major drawbacks of this type of process, one may mention the formation of highly toxic benzofuran compounds which appear to be even more hazardous than the PCBs themselves.

The usefulness of the process using lithium or sodium in the presence of alcohols and THF to dechlorinate non-aromatic organic compounds has been recognized in the prior art for many years. Hence, aliphatic halides, which are normally quite reactive compounds, especially when nucleophilic substitution or elimination of the halide ion is desired, have been dehalogenated using sodium or lithium in the presence of an alcohol and this type of reaction is well documented in text books as well as in other types of prior art publications.

Firstly, a number of basic organic chemistry textbooks describe dechlorination reactions involving lithium or sodium in the presence of alcohol and THF. In the third edition of "Advanced Organic Chemistry", March, at page 390, mentions that a good reducing agent for the removal of halogen atoms in a non-aromatic polyhalo compound (including vinyl, allylic, geminal, and even bridgehead halogens) is lithium or sodium and t-BuOH in tetrahydrofuran. Solomons, in the third edition of "Organic Chemistry", teaches the dehydrohalogenation of alkyl halides using a variety of strong bases such as the sodium salts of various alcohols.

In a similar fashion, Morrison and Boyd, in the fifth edition of "Organic Chemistry", describe a reaction for the dehalogenation of alkyl halides using potassium hydroxide and ethanol (pp. 265-266), as well as reactions for the dehydrohalogenation of vicinal dihalides also using potassium hydroxide with an alcohol (pp. 420-421). Morrison and Boyd also mention that typically, aryl halides undergo nucleophilic substitution only with extreme difficulty. The authors state that it is not possible to use aryl halides as alkyl halides are used, for example, in the Friedel-Crafts reaction (page 1034-1035).

It therefore appears from the textbooks referred to above that nucleophilic substitution of halides has been mainly performed on aliphatic halides, the same reaction being difficult to operate on aromatic halides. This finding is also exemplified in the following publications referring to dechlorination of various types of non-aromatic compounds.

Kornel et al., in "PCB destruction, a novel dehalogenation reagent", Journal of Hazardous Materials, 12 (1985), 161-176, describe the use of polyethylene glycol and sodium hydroxide in the dechlorination of PCBs at a temperature ranging from 60° to 100° C. According to the authors, alkali polyethylene glycolate complexes are mainly used because of their relative stability with regard to water and atmospheric oxygen. The process described by Kornel et al. involves the previous preparation of a dehalogenating agent which consists in mixing polyethylene glycol with potassium hydroxide and heating the solution until potassium hydroxide has fully dissolved. The reagent is then reacted with the PCB containing solution. Hence, the work of Kornel et al. mainly involves the use of alcoholic sodium hydroxide or polyethylene glycol/metal hydroxide in the dechlorination of PCBs.

In U.S. Pat. No. 4,377,471, Brown et al. disclose a process for dechlorinating PCBs that requires the use of sodium metal and an aprotic ion-complexing solvent amongst which a certain number of ethers such as ethylene glycol dimethyl ether may be selected. This process, which appears to be carried out at room temperature, does not appear to refer to or suggest the use of any alcohol solvent to perform the dechlorination of the PCB contaminated solution.

In U.S. Pat. No. 2,717,851 issued to Lidov and in U.S. Pat. No. 2,676,132 to Bluestone, the authors describe a process through which a chlorinated compound, such as heptachlorobicycloheptene, is treated with an ethanolic potassium hydroxide solution with the view to partially dechlorinate the given compound. Thus, the process described by Lidov leads to the removal of one chlorine atom on the heptachlorobicycloheptene molecule.

Griffin et al., in "Perchloro cage compounds. I. Structural Studies", Journal of Organic Chemistry, Vol. 29, 1964, pages 3192-3196, teach a process for dechlorinating chlorinated organics. The process involves reacting small pieces of metallic sodium with a solution comprising the compound to be dechlorinated along with t-butyl alcohol in tetrahydrofuran. The reaction appears to be performed at relatively low temperatures. The process described by Griffin is aimed at removing chlorine atoms from non-aromatic organic compounds.

Wilcox et al., in "The Synthesis of 1,4-dichlorobicyclo2.2.i]heptane", Journal of Organic Chemistry, August 1964, pages 2209-2211, describe a process by which a chlorinated compound is partly dechlorinated using lithium and t-butyl alcohol in tetrahydrofuran.

Soloway et al., in "Reactions of Isodrin and Endrin", Journal of American Chemical Society 82, (1960), pages 5377-5385, describe a method for dechlorinating non-aromatic compounds in n-amyl alcohol and xylene using sodium. Similarly, Stedman et al., in "The birdcage ketone, hexacyclo[5.4.1.0.0.0.0]dodecan-4-one, and some of its derivatives", Journal of Canadian Chemistry 32, (1967), pages 35-8, teach the dechlorination of non-aromatic chlorinated compounds using t-butyl alcohol and lithium wire cut into small pieces.

Von Doering et al., in "The addition of dichlorocarbene to olefins", Journal of American Chemical Society, (1954), pages 6162-6165, describe a dehalogenation process in which metallic sodium is used along with methanol. Methanol is added dropwise with rapid stirring after sodium has been added to the solution containing the halogenated compound to be reduced, the compound to be dechlorinated being a non-aromatic compound. The methanol used in this process is wet methanol.

In the Gassman et al. reference entitled "The chemistry of 7-substituted norbornenes. The reaction of bicyclo[2.2.1]hept-2-en-7-one with peracid", Journal of Canadian Chemistry, (1964), Vol. 29, pages 160-163, the authors describe a dehalogenation process using t-butyl in tetrahydrofurane with finely chopped lithium wire. The process is applied to non-aromatic compounds.

Hence, the prior art processes described above mostly refer to the use of sodium or lithium along with various alcohols to partially dehalogenate certain types of mainly halogenated compounds. In fact, most of the reactions carried out in these references are directed at selectively removing chlorine from certain positions in cyclic and acyclic aliphatic chlorides for the preparation of certain novel chemicals or for basic research. One obvious common factor among these references is that all the chlorinated compounds that have so far been treated are aliphatic, cyclic or acyclic. Aliphatic halides, as mentioned earlier in the Morrison and Boyd reference, are normally much more reactive than aromatic halides, particularly when nucleophilic substitution or elimination of the halide ion is concerned. In fact, some basic organic chemistry textbooks seem to suggest that reactions involving nucleophilic substitution of aryl halides are not desirable since they have to be conducted under harsh experimental conditions and since they are overall inefficient.

Therefore, the development of suitable alternatives to presently existing processes for dehalogenating haloaromatics, particularly for decontaminating methanolic extracts of PCB contaminated soil, methanol washings of PCB and Askarel containers, high concentration levels of PCB and Askarel in transformer oils and for treating neat PCBs and Askarel, would be highly desirable.

SUMMARY OF THE INVENTION

In accordance with the present invention, there is provided a process for the reductive dehalogenation of halogenated aromatics. The process comprises reacting halogenated aromatics with sodium or calcium in the presence of a lower alcohol such as methanol, ethanol or isopropanol, preferably methanol, to convert the halogenated aromatics to hydrogenated aromatics.

Preferably, the process of the present invention is performed under conditions whereby sodium is in melted form. The use of a lower alcohol such as methanol in the dehalogenation process avoids extensive polymerization from PCBs and polyhalogenated aromatics and also helps to prevent decomposition of the oil in which the substances to be dehalogenated may be found Thus, when it is desired to prevent oil decomposition, the use of methanol in quantities not exceeding half the molar amount of sodium was found to be desirable. By doing so, the oil is kept intact and even its color, a faint yellow, is not altered by the reaction. Furthermore, the major products formed under these conditions are those resulting from the dechlorination of PCBs such as biphenyl. On the other hand, the absence of methanol in a reaction mixture containing oil affords a viscous dark black gum resulting from the extensive decomposition of the oil and polymerization of the aromatic halides. In these instances, identification of the dechlorinated products is difficult.

When calcium is used as the dechlorinating agent, it is used in a commercially available form, that is in granular form or as turnings, in a lower alcohol, preferably methanol, at room temperature. However, there are, in this case, no specific molar ratio limitations between the metal and methanol. Hence, the reaction using calcium and methanol is suitable to dechlorinate PCBs or Askarel in methanol. It may be a one step process if it is desired to reduce the PCB concentration in a given PCB solution or as a repetitive two step process if it is desired to eliminate PCBs.

Ethanol and isopropanol can be used as suitable alcohols but for economical and performance considerations, methanol is the preferred alcohol. Also preferred is the use of a nitrogen atmosphere when performing the reaction with sodium.

The process of the present invention can therefore be employed to dehalogenate various types of PCBs or other polyhalogenated aromatics at various concentrations such as those found in transformer oils.

Some prior art literature refers to the use of alcoholic metal hydroxides such as NaOH/ROH in dehalogenation reactions. The present invention refers to the use of alkali or alkaline earth metal in alcohols (e g. Na—ROH). Hence, the process of the present invention is to be distinguished from other processes that require the use of alcoholic sodium hydroxide or polyethylene glycol/metal hydroxide. Basically, each reaction proceeds with different chemistry in terms of mechanisms and products.

The present invention will he more readily illustrated by referring to the following description.

DETAILED DESCRIPTION OF THE INVENTION

The present invention relates to a process useful to dehalogenate polyhaloaromatic compounds and particular)y to dechlorinate polychlorinated biphenyls present in transformer oil. It involves reacting halogenated aromatics in a lower alcohol such as methanol, ethanol or isopropanol with either sodium or calcium, preferably but not necessarily under a nitrogen atmosphere.

COMPOUNDS TO BE DEHALOGENATED

The process of the present invention may be used to dehalogenate a wide variety of halogenated aromatics at various concentrations. The process is to be employed mainly in the dechlorination of polychlorinated biphenyls (PCBs) although it is to be understood that it could be used in the reductive dehalogenation of other types of aromatic compounds.

METALS

Two types of metal are mainly contemplated for use in the process of the present invention. One metal, sodium, is an alkali metal and one metal, calcium, is an alkaline earth metal. The form in which the metals are used may vary depending on the nature of the metal itself.

In the case of sodium, if dehalogenation is conducted above the melting point of this metal, that is above 97° C., the form of the metal is not critical since sodium will be in a liquid, active form. At room temperature however, sodium must first be brought to its reactive sand form. It is to be noted that dehalogenation at room temperature normally requires longer reaction times and is less efficient than dehalogenation performed at temperatures above the melting point of sodium.

In the case of calcium, the temperature at which the reaction is performed and the form of the metal are not crucial factors in the reaction. In fact, calcium may be used in granular form or as turnings with methanol as the solvent.

ALCOHOLS

The alcohols that may be used in the context of the present invention are mainly lower alcohols such as methanol, ethanol and isopropanol. Methanol has been found to be the most suitable alcohol which could be used both in terms of cost and efficiency. However, ethanol and isopropanol are to be viewed as possible alternatives.

It is mostly preferred to use sodium and methanol as reactants in the dehalogenation process of the present invention. The starting sodium/methanol/halogen molar ratio may be in the following range: 30-40:-15-20:1. Further development has shown that a 2/1/1 ratio is the most practical ratio since it requires less sodium and affords evenly effective reaction conditions.

PROCESS

Reaction mechanism

It is believed that the dehalogenation of the present invention can proceed through two possible mechanisms. Thus, the reaction could possibly proceed through either an electron transfer/hydrogen abstraction mechanism that involves the formation of radical anions and radicals or through an abstraction/elimination mechanism that involves the formation of benzynes as reactive intermediates.

In the process of the present invention, similarly to other processes that require the use of metals such as sodium to dehalogenate polyhalogenated aromatics such as PCBs, the principal PCB dechlorination step involves an electron transfer process. As shown in Scheme 1 below, the metal transfers an electron to the aromatic halide, ArCl, to form a radical anion (I) which then looses a chloride ion to yield radical (II). Subsequently, radical (II) abstracts hydrogen to yield the desired dechlorinated product.

Scheme 1

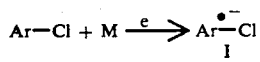

(1)

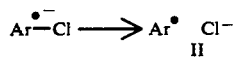

(2)

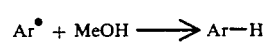

(3)

In addition to the general mechanism shown above that describes the involvement of radicals and radical anions in the dehalogenation process, it appears that other intermediates, such as benzyne, may also be involved.

As shown in Scheme II below, the strongly basic methoxide anion, MeO⁻, generated in situ from the reaction of methanol with the metal, may abstract hydrogen from one of the biphenyl rings in a PCB molecule (III) to produce anion (IV). Dechlorination of (IV) would then proceed by eliminating the chloride anion resulting in the formation of benzyne intermediate (V). The formation of such intermediate is made possible by the presence of several negative chlorine atoms on the aromatic rings of PCBs. These atoms, through their negative inductive effects, render the aromatic hydrogens slightly acidic thus favoring reaction with the strongly basic methoxide ion. Subsequent elimination of the chloride ion from (IV) gives the benzyne intermediate (V). Repetition of this abstraction/elimination process would thus lead to another effective route for PCB dechlorination.

Scheme 2

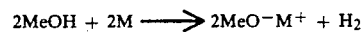

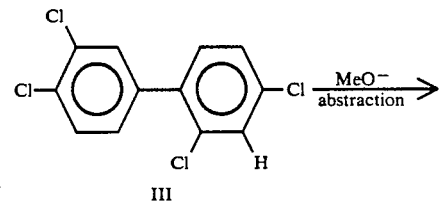

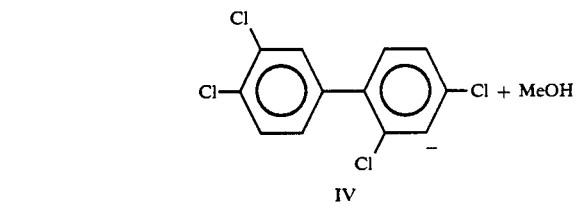

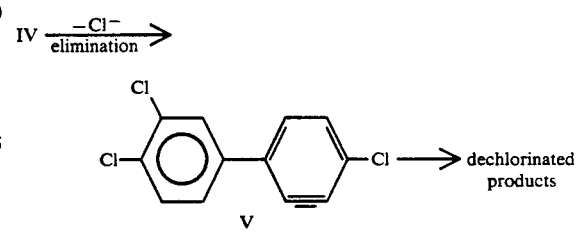

It is to be noted that this second mechanism is not fully understood and that its validity with regard to the present system is uncertain. A very strong base such as an amide anion (NH₂⁻) is normally required to generate benzyne from aromatic halides. However, the presence of several chlorine atoms (as election with drawing groups) or PCBs may render some hydrogens on the ring acidic enough to react with the weaker base methoxide anion to give (IV).

(a) When using sodium

If sodium is to be employed as the principal active component in the process, a suitable vehicle such as transformer oil is first used to melt the sodium at a temperature of about 100° C. in order to transfer it into one of its most reactive forms. As mentioned earlier, the sodium particle size is not critical.

Once sodium has been brought to its melted form in the transformer oil, the dechlorination process is carried out at approximately the same temperature as the melting point of sodium, thus allowing sodium to stay in its reactive form. One of the alcohols referred to above is used to stop polymerization from taking place and to stop the decomposition of the oil which can be recycled and used again. The alcohol that is preferred is methanol. The use of an inert gas is important, for safety considerations. However, the reaction proceeds in the absence of inert atmosphere.

In the absence of alcohol, particularly methanol, but under otherwise identical conditions, dehalogenation takes place with a smaller amount of sodium, that is approximately half the amount required when an alcohol is present. However, under these conditions, dehalogenation is often accompanied with oil destruction and extensive polymerization, particularly from the biphenyls present in the solution.

It is important to note that sodium is the preferred metal to be used. When similar dehalogenation is attempted with lithium metal instead of sodium under otherwise identical conditions, the halogenated aromatics remain almost intact with very little dehalogenation taking place. If THF is added to a PCB mixture contained in oil and substantial heat is applied to the process, that is a temperature over 170° C. for a period exceeding 17 hours, more than 25% of the original concentration of the halogenated aromatics remain intact.

In fact, it is the presence of oil that apparently reduces the reactivity of lithium. If no oil is present in the PCB mixture, Li can be used to dechlorinate PCBs in a suitable organic solvent such as THF. However, the use of THF is not recommended for commercial use because of the following factors: it is corrosive, hazardous, expensive and undesirable because of the significant side reaction that takes place between lithium and THF. In fact, in some instances, lithium placed in contact with a solution containing PCBs, THF and oil will react with THF but not with the PCBs.

Thus, numerous advantages result from the use of a lower alcohol such as methanol in a dehalogenation process. Hence, methanol apparently participates in the reduction process. It also appears to prevent oil decomposition and leads to a clean formation of biphenyl products while reducing the possibility of polymer formation. Also, the low cost of methanol renders the process readily feasible commercially.

The reaction described above can proceed using various conditions. Firstly, different temperatures may be used. The reaction has been found to proceed at room temperature but the speed of the reaction is increased if the temperature is above the melting point of sodium. Also, the reaction time may range between 1 and 24 hours. Furthermore, different concentrations of halogenated aromatics can be treated under the conditions set forth above. For example, concentrations of over 100,000 ppm of PCBs can be easily treated using the method of the present invention. It is to be understood, however, that concentrations below the 100,000 ppm mark can also be treated.

The process is particularly useful to treat methanolic extracts of PCB contaminated soil, methanol washings of PCB and Askarel containers, PCB and Askarel in transformer oil as well as neat Askarel.

b) when using calcium

When it is desired to use calcium in the dehalogenation process of the present invention, calcium is to be added to a mixture containing the halogenated aromatics in a lower alcohol such as methanol at a temperature close to room temperature. Other types of alcohols such as ethanol and isopropanol could also be used to perform the dehalogenation using calcium, provided that methanol is present.

The following examples are provided to illustrate rather than limit the scope of the present invention.

EXAMPLE 1

Reductive dechlorination of Askarel using sodium in methanol 2.01 g of sodium were heated in 50 ml of transformer mineral oil at a temperature of 105° C. After having melted sodium, the mixture was rapidly stirred to transfer sodium into a very reactive sand form. The oil was then carefully cooled down so that sodium could stay in its reactive sand form. 1.040 g of Askarel (Arochlor 1260 (40%) in trichlorobenzenes) in 1.410 g of methanol was added to the above mixture under nitrogen and the reaction mixture was heated just above the melting point of sodium for 30 minutes. Under these conditions, sodium stayed as a fine powder in a very reactive form. The mixture was then cooled down to room temperature so that the reaction vessel could be agitated to get the chlorinated aromatics from the wall of the flask into the reacting area. The mixture, pink in color, was heated for another 30 minutes and a yellow color was obtained. At this stage, a sample was withdrawn from the reaction mixture and analyzed by GC/ECD. After quenching with water, clean up with acid and extraction with hexane, the GC/ECD showed complete disappearance of the 20,800 ppm Askarel that was originally present in the oil. An external standard of 1 ppm Arochlor 1260 was used to monitor the dechlorination process. GC/ECD analysis showed no presence of Askarel after treatment. Furthermore, chloride analysis by HFLC ion chromatography showed complete recovery of the organo-chlorine in Askarel as sodium chloride.

EXAMPLE 2

When sodium was replaced by lithium, under conditions otherwise similar to those of Example 1, no reaction was observed. It is only when the reaction mixture was heated above 150° C. that only about 70% of the PCBs in Askarel were degraded. The presence of the transformer oil seems to deactivate lithium which otherwise is known to dehalogenate aromatic halides in polar solvents.

Thus, when mixing lithium (1.128 g, 0.16 mole) and Askarel (1.6718 g) 1n transformer mineral oil (50 ml) containing methanol (2.58 g) at room temperature, no reaction was observed. When the mixture was heated for 2 hours at 105° C., no reaction was observed. The mixture was then heated between 150° and 175° C. for 2 hours. It is after this drastic heating that only about 70% of the Arochlor 1260 in Askarel disappeared. This example demonstrates the necessity to use sodium as an alkali metal in the process of the present invention.

EXAMPLE 3

Dechlorination of Arochlor 1248 using calcium in methanol

To 0.23 9 of Arochlor 1248 in 100 ml of methanol, 2.0 g of calcium were added under a nitrogen atmosphere at room temperature. The mixture was then stirred and an immediate reaction took place. After the disappearance of calcium, that is approximately 40 minutes, a 200 ul sample was taken out, neutralized with 0.5 ml of water and then extracted with 1 ml of hexane. GC analysis indicated disappearance of about 50% of the PCBs. The reaction mixture was then subjected to a second treatment outlined as follows.

Unreacted PCBs and their organic products were extracted into 2×100 ml of hexane and hexane was subsequently evaporated on a water pump at room temperature to avoid loss of PCBs. The residual untreated PCBs were dissolved in 100 ml of methanol and treated with 2.01 g of calcium for 1 hour at room temperature. The reaction mixture was worked up as described above. GC and GC/MS analysis showed disappearance of more than 95% of the PCBs whereas biphenyl (m/e 154), mono-chlorobiphenyl (m/e 188) and di-chlorobiphenyl (m/e 122) formed in almost equal amounts.

EXAMPLE 4

Dechlorination of Askarel

The conditions cited in Example 3 for the dechlorination of Arochlor 1248 were repeated for the dechlorination of Askarel. To a mixture of Askarel (1.5990 g) in methanol (100 ml), 2.04 g of calcium were added and the mixture was stirred at room temperature until calcium metal disappeared. Hexane extraction was then performed to prepare unreacted Askarel for the second treatment. The second treatment also involved the use of 2.04 g of calcium and 100 ml of methanol. After the disappearance of calcium GC/Mass analysis indicated that close to 99% of Askarel had disappeared. The products formed were mainly biphenyl and partially hydrogenated mono- and di-chlorobiphenyls, traces of cyclohexylbenzene and cyclohexenylbenzene are also formed.

EXAMPLE 5

When the experimental conditions of Examples 3 and 4 were used replacing methanol with iso-propanol and terbutanol or THF, no appreciable dechlorination was observed.

We claim:

1. A process for the reductive dehalogenation of halogenated aromatics, said process comprising reacting halogenated aromatics with calcium in a solvent selected from the group consisting of methanol, ethanol and isopropanol and mixtures thereof and recovering the products resulting from the reduction of said halogenated aromatics.

2. A process according to claim 1, wherein said solvent is methanol.

3. A process according to claim 1, wherein said calcium is used in granular form or as turnings.

4. A process according to claim 1, wherein said dehalogenation reaction is carried out at room temperature.

5. A process according to claim 1, where said halogenated aromatics are polychlorinated biphenyls.

6. A process according to claim 1, wherein said halogenated aromatics are contained in soil.

7. A process for the treatment of soil contaminated with halogenated aromatics to dehalogenate said halogenated aromatics, said process comprising:
preparing a methanolic extract of said soil;
reacting said extract with calcium; and
recovering the products resulting from the dehalogenation of said halogenated aromatics.

8. A process according to claim 7, wherein said calcium is granula for or as turnings.

9. A process according to claim 7, wherein said reaction is carried out at room temperature.

10. A process according to claim 7, wherein said halogenated aromatics are polychlorinated biphenyls.

* * * * *

UNITED STATES PATENT AND TRADEMARK OFFICE
CERTIFICATE OF CORRECTION

PATENT NO. : 5,185,488
DATED : February 9, 1992
INVENTOR(S) : Jalal A. Hawari, et al It is certified that error appears in the above-indentified patent and that said Letters Patent is hereby corrected as shown below:

On the title page, Item

(73) Assignee: Majesty (Her) in right of Canada as represented by The National Research Council of Canada Column 10, Claim 8, line 39, after "is", delete "granula for" and insert therefor --used in granular form--.

Signed and Sealed this

First Day of March, 1994

Attest:

BRUCE LEHMAN

Attesting Officer

Commissioner of Patents and Trademarks